(12) United States Patent
Ribble

(10) Patent No.: US 10,172,522 B2
(45) Date of Patent: *Jan. 8, 2019

(54) PATIENT-NEED PREDICTION SYSTEM

(71) Applicant: Hill-Rom Services, Inc., Batesville, IN (US)

(72) Inventor: David L. Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,876

(22) Filed: Sep. 15, 2017

(65) Prior Publication Data

US 2018/0020924 A1 Jan. 25, 2018

Related U.S. Application Data

(63) Continuation of application No. 15/091,922, filed on Apr. 6, 2016, now Pat. No. 9,763,576, which is a (Continued)

(51) Int. Cl.
*A61B 5/00* (2006.01)
*A61B 5/01* (2006.01)
(Continued)

(52) U.S. Cl.
CPC .............. *A61B 5/0077* (2013.01); *A61B 5/01* (2013.01); *A61B 5/1032* (2013.01); *A61B 5/1113* (2013.01); *A61B 5/1128* (2013.01); *A61B 5/6892* (2013.01); *A61B 5/7275* (2013.01); *A61B 5/7282* (2013.01); *A61B 5/742* (2013.01); *A61B 5/7405* (2013.01); *A61B 5/7465* (2013.01); *A61B 5/7475* (2013.01); *A61G 7/0524* (2016.11); *G06F 19/00* (2013.01);
(Continued)

(58) Field of Classification Search
CPC ....... A61B 5/0077; A61B 5/01; A61B 5/1032; A61B 5/1113; A61B 5/1128; A61B 5/7275; A61B 5/7282; A61B 5/7465; G08B 21/0453; G08B 21/22; G06F 19/3418; G06F 19/327; G06F 19/345; G06Q 50/22
USPC ...................................... 340/573.5
See application file for complete search history.

(56) References Cited

U.S. PATENT DOCUMENTS 3,972,320 A 8/1976 Kalman et al.
4,196,425 A 4/1980 Weekly et al.
(Continued)

FOREIGN PATENT DOCUMENTS

KR 20090001848 A 1/2009
WO 2002075688 A2 9/2002

OTHER PUBLICATIONS

EP Search Report for related EP application 15162821, dated Oct. 16, 2017, 7 pages.
(Continued)

*Primary Examiner* — John A Tweel, Jr.
(74) *Attorney, Agent, or Firm* — Barnes & Thornburg LLP

(57) ABSTRACT

A patient support apparatus includes a control system operable to gather physiological information about a patient supported on the patient support apparatus. The information may be gathered from sensors, a user interface, or a hospital information system. The control system uses the data gathered to predict whether a patient is likely to be in need of care from a caregiver.

22 Claims, 5 Drawing Sheets

Related U.S. Application Data continuation of application No. 14/250,848, filed on Apr. 11, 2014, now Pat. No. 9,311,804.

(51) Int. Cl.
| | | |
|---|---|---|
| *G08B 21/04* | (2006.01) | |
| *A61B 5/11* | (2006.01) | |
| *G08B 21/22* | (2006.01) | |
| *G06Q 50/22* | (2018.01) | |
| *G06F 19/00* | (2018.01) | |
| *A61B 5/103* | (2006.01) | |
| *A61G 7/05* | (2006.01) | |
| *G16H 40/20* | (2018.01) | |
| *G16H 50/20* | (2018.01) | |

(52) U.S. Cl.
CPC ......... *G06F 19/3418* (2013.01); *G06Q 50/22* (2013.01); *G08B 21/0453* (2013.01); *G08B 21/22* (2013.01); *A61B 2562/0247* (2013.01); *G16H 40/20* (2018.01); *G16H 50/20* (2018.01)

(56) References Cited

U.S. PATENT DOCUMENTS

| | | | |
|---|---|---|---|
| 4,539,560 A | 9/1985 | Fleck et al. | |
| 4,633,237 A | 12/1986 | Tucknott et al. | |
| 4,814,751 A | 3/1989 | Hawkins et al. | |
| 4,907,845 A | 3/1990 | Wood et al. | |
| 4,947,152 A | 8/1990 | Hodges et al. | |
| 4,952,928 A | 8/1990 | Carroll et al. | |
| 5,008,654 A | 4/1991 | Callaway et al. | |
| 5,107,854 A | 4/1992 | Knotts et al. | |
| 5,218,344 A | 6/1993 | Ricketts | |
| 5,276,432 A | 1/1994 | Travis et al. | |
| 5,353,012 A | 10/1994 | Barham et al. | |
| 5,365,217 A | 11/1994 | Toner et al. | |
| 5,416,695 A | 5/1995 | Stutman et al. | |
| 5,495,288 A | 2/1996 | Broady et al. | |
| 5,519,380 A | 5/1996 | Edwards et al. | |
| 5,583,758 A | 12/1996 | McIlroy et al. | |
| 5,633,627 A | 5/1997 | Newham | |
| 5,714,931 A | 2/1998 | Petite et al. | |
| 5,738,102 A | 4/1998 | Lemelson et al. | |
| 5,740,800 A | 4/1998 | Hendrickson et al. | |
| 5,765,139 A | 6/1998 | Bondy et al. | |
| 5,780,798 A | 7/1998 | Hall-Jackson et al. | |
| 5,781,442 A | 7/1998 | Engleson et al. | |
| 5,831,699 A | 11/1998 | Wright et al. | |
| 5,844,488 A | 12/1998 | Musick | |
| 5,877,675 A | 3/1999 | Rebstock et al. | |
| 5,946,659 A | 8/1999 | Lancelot et al. | |
| 5,953,704 A | 9/1999 | McIlroy et al. | |
| 6,049,281 A | 4/2000 | Osterweil et al. | |
| 6,067,019 A | 5/2000 | Scott et al. | |
| 6,078,261 A | 6/2000 | Davsko et al. | |
| 6,125,350 A | 9/2000 | Dirbas et al. | |
| 6,154,139 A | 11/2000 | Heller | |
| 6,160,478 A | 12/2000 | Jacobsen et al. | |
| 6,204,767 B1 | 3/2001 | Sparks | |
| 6,259,355 B1 | 7/2001 | Chaco et al. | |
| 6,402,691 B1 | 6/2002 | Peddicord et al. | |
| 6,433,690 B2 | 8/2002 | Petelenz et al. | |
| 6,466,125 B1 | 10/2002 | Richards et al. | |
| 6,524,239 B1 | 2/2003 | Reed et al. | |
| 6,544,200 B1 | 4/2003 | Smith et al. | |
| 6,583,727 B2 | 6/2003 | Nunome | |
| 6,611,206 B2 | 8/2003 | Eshelman et al. | |
| 6,611,783 B2 | 8/2003 | Kelly, Jr. et al. | |
| 6,624,754 B1 | 9/2003 | Hoffman et al. | |
| 6,640,212 B1 | 10/2003 | Rosse | |
| 6,674,403 B2 | 1/2004 | Gray et al. | |
| 6,748,250 B1 | 6/2004 | Berman et al. | |
| 6,753,783 B2 | 6/2004 | Friedman et al. | |
| 6,788,206 B1 | 9/2004 | Edwards | |
| 6,791,460 B2 | 9/2004 | Dixon et al. | |
| 6,804,656 B1 | 10/2004 | Rosenfeld et al. | |
| 6,821,258 B2 | 11/2004 | Reed et al. | |
| 6,822,571 B2 | 11/2004 | Conway | |
| 6,830,180 B2 | 12/2004 | Walsh | |
| 6,838,992 B2 | 1/2005 | Tenarvitz | |
| 6,853,304 B2 | 2/2005 | Reisman et al. | |
| 6,876,303 B2 | 4/2005 | Reeder et al. | |
| 6,897,781 B2 | 5/2005 | Cooper et al. | |
| 6,900,732 B2 | 5/2005 | Richards | |
| 6,909,367 B1 | 6/2005 | Wetmore | |
| 6,915,170 B2 | 7/2005 | Engleson et al. | |
| 6,941,239 B2 | 9/2005 | Unuma et al. | |
| 6,958,706 B2 | 10/2005 | Chaco et al. | |
| 6,968,294 B2 | 11/2005 | Gutta et al. | |
| 6,975,230 B1 | 12/2005 | Brilman | |
| 6,987,232 B2 | 1/2006 | Smith et al. | |
| 7,001,334 B2 | 2/2006 | Reed et al. | |
| 7,035,432 B2 | 4/2006 | Szuba | |
| 7,071,820 B2 | 7/2006 | Callaway | |
| 7,110,569 B2 | 9/2006 | Brodsky et al. | |
| 7,200,894 B2 | 4/2007 | Block et al. | |
| 7,242,306 B2 | 7/2007 | Wildman et al. | |
| 7,369,680 B2 | 5/2008 | Trajkovic et al. | |
| 7,437,787 B2 | 10/2008 | Bhai | |
| 7,452,336 B2 | 11/2008 | Thompson | |
| 7,502,498 B2 | 3/2009 | Wen et al. | |
| 7,505,620 B2 | 3/2009 | Braune et al. | |
| 7,609,059 B2 | 10/2009 | Hughes | |
| 7,987,069 B2 | 7/2011 | Rodgers et al. | |
| 7,988,647 B2 | 8/2011 | Bunn et al. | |
| 8,620,625 B2 | 12/2013 | Sing et al. | |
| 8,907,287 B2 | 12/2014 | Vanderpohl | |
| 9,311,804 B2 * | 4/2016 | Ribble | G08B 21/0453 |
| 9,763,576 B2 | 9/2017 | Ribble | |
| 2002/0140559 A1 | 10/2002 | Zhou et al. | |
| 2002/0165733 A1 | 11/2002 | Pulkkinen et al. | |
| 2003/0013459 A1 | 1/2003 | Rankin et al. | |
| 2003/0114736 A1 | 6/2003 | Reed et al. | |
| 2005/0251914 A1 | 11/2005 | Schaller et al. | |
| 2008/0189865 A1 | 8/2008 | Bhai | |
| 2008/0294012 A1 | 11/2008 | Kurtz et al. | |
| 2009/0229051 A1 | 9/2009 | Heimbrock et al. | |
| 2009/0275808 A1 | 11/2009 | DiMaio et al. | |
| 2010/0124737 A1 | 5/2010 | Panzer | |
| 2011/0152727 A1 | 6/2011 | Ten Kate | |
| 2011/0278459 A1 | 11/2011 | Hohl et al. | |
| 2013/0127620 A1 | 5/2013 | Siebers et al. | |
| 2013/0246088 A1 | 9/2013 | Huster et al. | |
| 2015/0109442 A1 | 4/2015 | Derenne et al. | |
| 2015/0141838 A1 | 5/2015 | Vanderpohl | |

OTHER PUBLICATIONS

Machine translation of KR20090001848A provided by the KIPO on Jan. 16, 2018; 13 pages.

\* cited by examiner

PATIENT-NEED PREDICTION SYSTEM

CROSS-REFERENCE TO RELATED U.S. APPLICATION

This application is a continuation of U.S. application Ser. No. 15/091,922, filed Apr. 6, 2016, now U.S. Pat. No. 9,763,576, which is a continuation of U.S. application Ser. No. 14/250,848, filed Apr. 11, 2014, now U.S. Pat. No. 9,311,804, each of which is expressly incorporated by reference herein.

BACKGROUND

The present application is related to a patient support apparatus, and more particularly to a patient support apparatus that includes a control system configured to control various components included in the patient support apparatus. More particularly, the patient support apparatus includes a sensor configured to provide data related to a patient resting on the patient support apparatus to the control system to cause the control system to perform a predetermined action in response to receiving the data.

Patients in a care facility such as a hospital, for example, require varying degrees of interaction with caregivers. Some patients may have full mobility while other patients may have reduced mobility. Certain protocols may be established for those patients identified as having limited mobility or a risk of falling. Such protocols may reduce the opportunity for patients to move about the patient room unassisted. One such protocol may require a caregiver to provide assistance to patients as patients move to and from the toilet to perform a toileting activity (urinate or defecate). Caregivers provide help to patients to minimize a risk of falling as the patient moves to and from the toilet as well as provide help should a fall occur.

The need for patients to use the toilet frequently causes caregivers to spend significant amounts of time dealing with the toileting activities of patients. In one example, a caregiver must move from one patient room to a remote patient room in response to a nurse call initiated by a patient who desires to use the toilet. Caregivers may prioritize support of planned toileting activities because of the potential risk of fall, increased risk of an incontinence event, increase risks to skin health due to incontinence events, and the significant amount of time required to respond to and deal with incontinence events.

SUMMARY

The present application discloses one or more of the features recited in the appended claims and/or the following features which alone or in any combination, may comprise patentable subject matter.

In one aspect of the present disclosure, a patient-need prediction system includes a sensor unit and a controller. The sensor unit is configured to detect electromagnetic radiation from a field of view and provide a sensor signal indicative of a characteristic of a patient in the field of view. The controller is coupled to the sensor unit and configured to process the sensor signal to produce a value related to stress experienced by a patient located in the field of view as detected by the sensor unit. The controller is further configured to determine whether the value has exceeded a predetermined limit and perform a predetermined action if the value has exceeded the predetermined limit.

In some embodiments, the electromagnetic radiation may be visual light. The sensor unit may detect the visual light over time.

In some embodiments, the field of view may be limited to a face of the patient in the field of view. The sensor unit may be configured to detect changes in facial expressions of the patient indicative of the stress condition.

In some embodiments, the sensor unit may detect changes in color of a patient's skin. The changes in color may be indicative of the stress condition.

In some embodiments, the sensor unit may detect changes in position of the patient in the field of view. The changes in position of the patient may be indicative of the stress condition.

In some embodiments, the stress condition may be a need to urinate by the patient. The stress condition may also be a need to defecate by the patient.

In some embodiments, the electromagnetic radiation is infrared light. The infrared light may be indicative of a patient's skin temperature.

In some embodiments, the sensor unit may be a camera. The camera may be located in spaced-apart relation to a patient in the field of view.

In some embodiments, the patient-need prediction system may further comprise a bed sensor unit. The bed sensor unit may be configured to provide a bed-sensor signal indicative of a status of equipment included in a patient support apparatus supporting the patient.

In some embodiments, the controller may be coupled to the bed sensor unit. The controller may be configured to process the bed-sensor signal and the sensor signal to produce the value related to stress experienced by the patient located in the field of view as detected by the sensor unit.

In some embodiments, the patient support apparatus may include a support frame, a support surface supported by the support frame, and a movable side rail coupled to the frame to move relative to the frame between a raised position and a lowered position. The bed-sensor signal may be indicative of the position of the movable siderail.

In some embodiments, the patient support apparatus may include a support frame and a support surface supported by the support frame. The bed-sensor signal may be indicative of a pressure exerted on the support surface when the patient is resting on the support surface.

In some embodiments, the patient-need prediction system may further comprise a communication link coupled to the controller. The communication link may communicate with a hospital information system. The predetermined action may include requesting via the communication link for a caregiver to come to the patient within a predetermined time period.

In some embodiments, the patient-need prediction system may further comprise a user interface coupled to the controller. The predetermined action may include communicating via the user interface to the patient that a caregiver has been requested to come to the patient within the predetermined time period.

In some embodiments, the communication may be visual and displayed on a display. The display may be included in the user interface.

In some embodiments, the communication may be auditory and emitted through a speaker. The speaker may be included in the user interface.

In some embodiments, the patient-need prediction system may further comprise a light coupled to the controller. The predetermined action may include commanding the light to emit light.

In another aspect of the present disclosure, a patient-need prediction system comprises a patient sensor and a patient support apparatus. The patient sensor unit may be configured to detect electromagnetic radiation from a field of view and provide a patient sensor signal indicative of a characteristic of a patient in the field of view. The patient support apparatus is adapted to support a patient thereon. A portion of the patient support apparatus is located in the field of view. The patient support apparatus includes a controller coupled to the patient sensor unit to receive the patient sensor signal to produce a value related to stress experienced by a patient located in the field of view as detected by the sensor unit. The controller is further configured to determine whether the value has exceeded a predetermined limit and perform a predetermined action if the value has exceeded the predetermined limit.

In some embodiments, the patient support apparatus may further include a bed sensor unit. The bed sensor unit may be configured to provide a bed-sensor signal indicative of a status of equipment included in a patient support apparatus supporting the patient.

In some embodiments, the controller may be coupled to the bed sensor unit. The controller may be configured to process the bed-sensor signal and the patient sensor signal to produce the value related to stress experienced by the patient located in the field of view as detected by the sensor unit.

In some embodiments, the patient support apparatus may include a support frame, a support surface supported by the support frame, and a movable siderail coupled to the frame to move relative to the frame between a raised position and a lowered position. The bed-sensor signal may be indicative of the position of the movable siderail.

In some embodiments, the patient support apparatus may include a support frame and a support surface supported by the support frame. The bed-sensor signal may be indicative of a pressure exerted on the support surface when the patient is resting on the support surface.

In some embodiments, the electromagnetic radiation may include visual light. The patient sensor unit may detect changes in facial expressions of the patient indicative of the stress condition.

In some embodiments, the electromagnetic radiation may further include infrared light. The patient sensor may detect changes in heat emitted from a patient's skin that is indicative of the stress condition. The stress condition may be at least one of a need to urinate and defecate by the patient.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
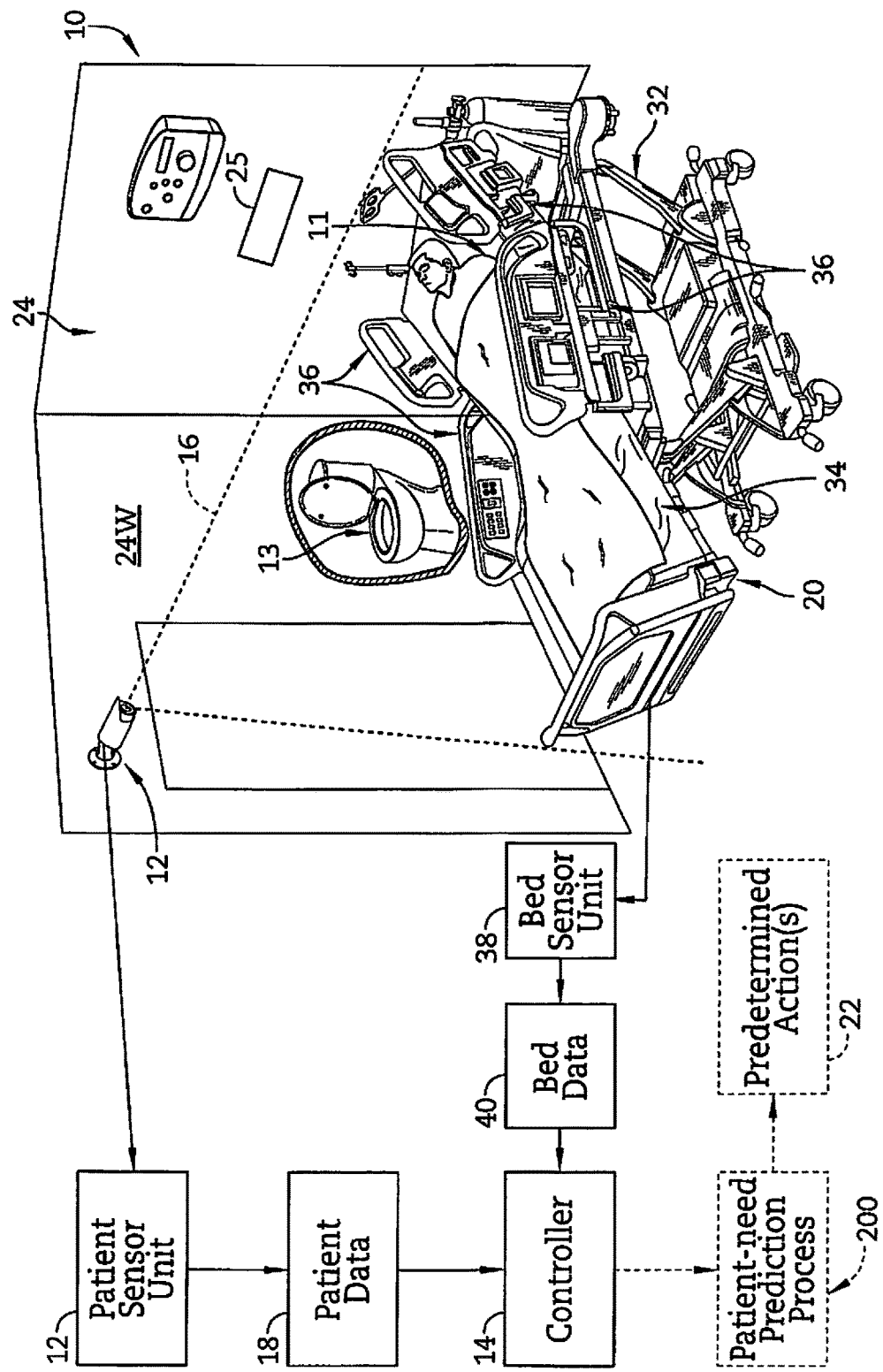
FIG. 1 is a diagrammatic view and partial perspective view of a first embodiment of a patient-need prediction system in accordance with the present disclosure showing that the patient-need prediction system cooperates with a patient support apparatus positioned in a room with a toilet to predict patient need.
Figure 2:
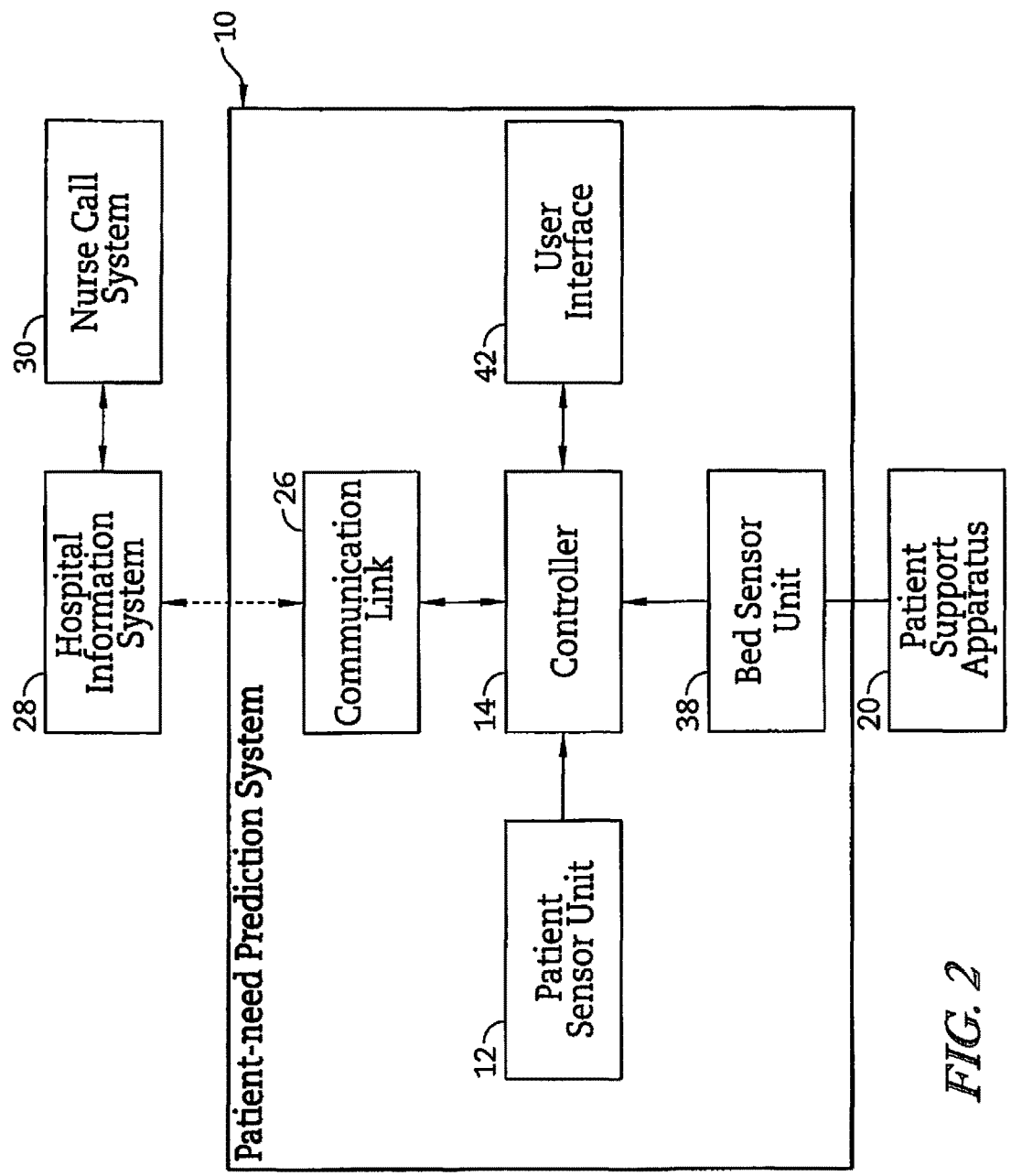
FIG. 2 is a diagrammatic view of the patient-need prediction system of FIG. 1.
Figure 4:
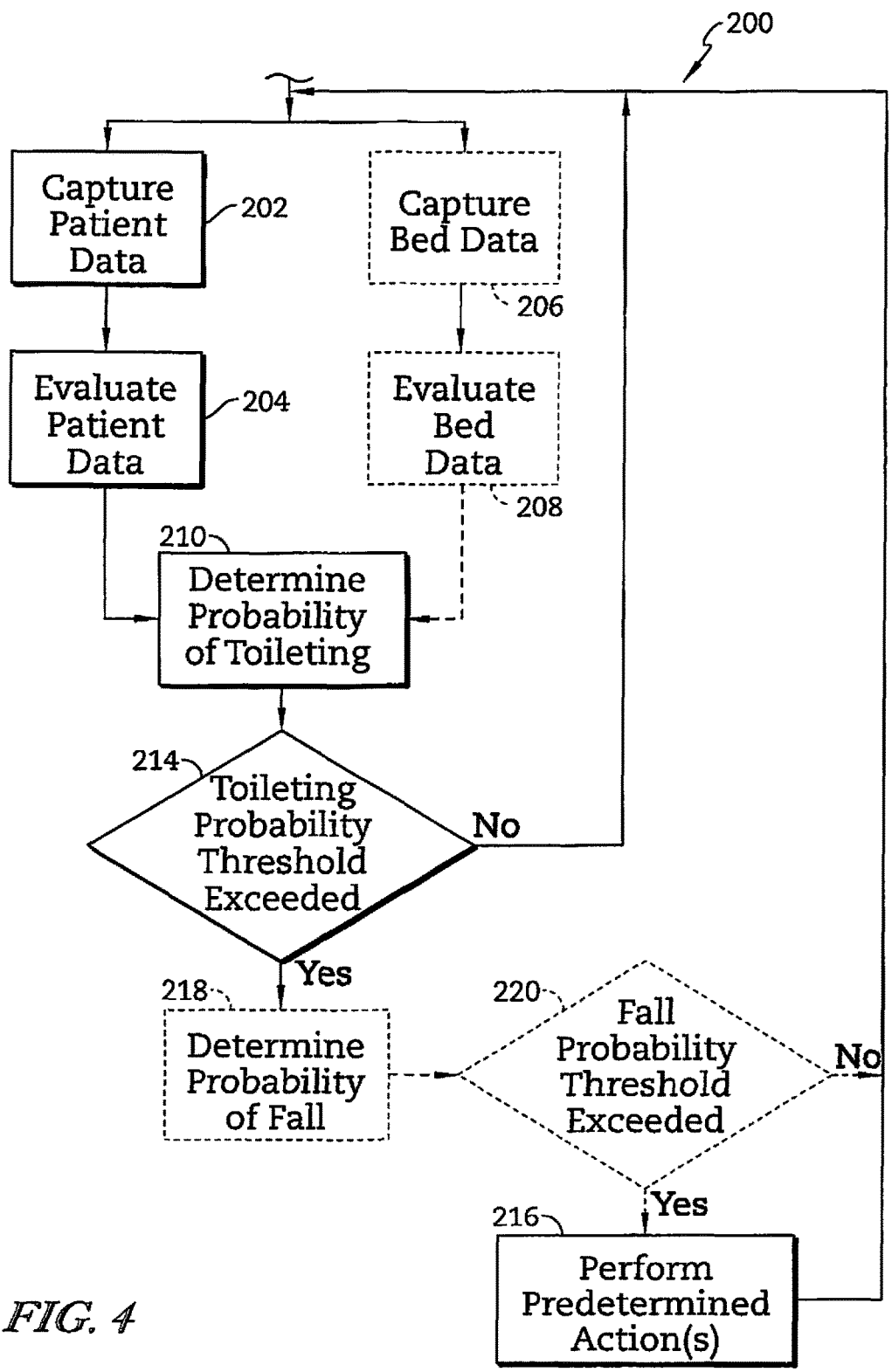
FIG. 4 is diagrammatic view of a process used by the patient-need prediction system to predict patient need and perform predetermined actions in response to predicted patient need.

A first embodiment of a patient-need prediction system 10 in accordance with the present disclosure is shown in FIGS. 1 and 2. A second embodiment of a patient-need prediction system 110 in accordance with the present disclosure is shown, for example, in FIG. 5. Both patient-need prediction systems 10, 110 include a controller 14, 114 configured to executed a patient-need prediction process 200 as shown in FIG. 4. The patient-need prediction system 10, 110 receives data from one or more sources and determines a probability that a patient 11 will have a need in a near term, for example, to use a toilet 13 included in a patient room 24. If the patient is predicted to have a near-term need, process 200 may execute a predetermined action so as to minimize risks associated with the patient's need as suggested in FIG. 4.

The patient-need prediction system 10 includes a patient sensor unit 12 and the controller 14 as shown, for example, in FIGS. 1 and 2. The patient sensor unit 12 is positioned to lie in spaced-apart relation to the patient 11 to detect electromagnetic radiation from a field 16 of view in which the patient 11 is located. The patient sensor unit 12 then converts the detected electromagnetic radiation into a patient sensor signal which is indicative of patient data 18 as shown in FIG. 1. The patient sensor signal is then communicated to the controller for processing to predict if the patient 11 will have near-term need. In one illustrative example, the patient sensor unit 12 is coupled to a wall 24W of a patient room in spaced-apart relation to the patient 11. The patient sensor unit 12 may communicate with the controller 14 via a wired connection or a wireless connection.

In one illustrative example, the patient sensor unit 12 includes a camera configured to detect visible electromagnetic radiation. In another example, the patient sensor unit 12 includes an infrared camera configured to detect infrared electromagnetic radiation. In still yet another example, the patient sensor unit 12 includes both a camera and an infrared camera.

The controller 14 is coupled to the patient sensor unit 12 to receive the patient sensor signal as suggested in FIG. 1. The controller 14 may be located in spaced-apart relation to the patient 11 or included in a patient support apparatus 20 which supports the patient 11. In one example, the controller 14 is coupled to the patient support apparatus 20 to command the patient support apparatus to perform one or more predetermined actions in response to receiving and processing the patient sensor signal. The patient sensor unit 12 may sense a change in a characteristic of the patient 11 which is predictive of a patient's need to perform a toileting activity (urinate or defecate) within a future time period. As a result, the controller 14 performs a predetermined action 22 as suggested in FIG. 1. The predetermined action 22 is, for example, to turn on a light 25 in a patient room 24.

In one example, the patient-need prediction system 10 may predict patient need before the patient 11 is even aware that they will have a need. The future time period may be as long as several minutes into the future. As a result, the patient-need prediction system 10 may determine that the patient 11 will have need to perform a toileting activity while the patient 11 may still be sleeping. The patient sensor unit 12 is configured to detect the patient's physiological response to a need to perform a toilet activity even when the patient 11 is non conscious.

The patient-need prediction system 10 further includes a communication link 26 as shown in FIG. 2. The communication link 26 is coupled to the controller 14 and configured to provide communication between the controller 14 and a hospital information system 28. The hospital information system 28 includes, for example, a centralized nurse call system 30 and a centralized electronic medical record system. Both the nurse call system 30 and electronic medical records system include information that is related to the patient support apparatus 20 and associated with the patient 11 stored in memory as related records. The information related to the patient 11 stored in memory in the nurse call system 30 and electronic medical records system is constantly updated as information is added to the electronic medical records system and the nurse call system 30 receives information related to the patient 11, the patient support apparatus 20, and the patient-need prediction system 10. In one example, the patient-need prediction system 10 may communicate the predicted need to the hospital information system 28 via the communication link 26. The hospital information system 28 in turn stores the event in the patient's electronic medical record. In another example, the hospital information system 28 requests that a caregiver come to the patient 11 to help with the predicted patient need.

The patient 11, as shown in FIG. 1, is supported on the patient support apparatus 20. The patient support apparatus 20 includes a support frame 32, a patient support surface 34, and one or more side rails 36. Together the support frame 32, the patient support surface 34, and the side rails 36 cooperate to maximize patient comfort and patient safety. The patient support surface 34 is coupled to the support frame 32 and located between the patient 11 and the support frame 32 to maximize patient comfort and minimize skin damage of the patient 11. The side rails 36 are coupled to the support frame 32 to move between lowered positions and raised positions. The lower positions are associated with the providing patient care or patient ingress and egress. The raised positions are associated with blocking patient ingress and egress.

The patient-need prediction system 10 further includes a bed sensor unit 38 as suggested in FIG. 1 and shown in FIG. 2. The bed sensor unit 38 is coupled to the patient support apparatus 20 and configured to provide a bed sensor signal to the controller 14. The bed sensor signal is indicative of bed data 40 as shown in FIG. 1. Bed data may include, for example, an arrangement of the support frame 32, a status of the patient support surface 34, and the positions of the side rails 36. The controller 14 receives the bed sensor signal and uses the bed data to improve a prediction of patient need. The controller 14 may also use the bed data to determine a risk of falling for the patient 11 which may alter the predetermined action performed by the controller 14. The controller 14 may also receive data from the hospital information system 28 which may affect the prediction of patient need and evaluation of risk of falling as suggested in FIG. 4.

As shown, for example, in FIG. 2, the patient-need prediction system 10 may further include a user interface 42. The user interface 42 is coupled to the controller 14 and configured to provide input data to the controller 14 and receive commands from the controller 14. In one example, the controller 14 may have predicted that the patient 11 will need help with a toileting activity. The controller 14 then commands the user interface 42 to display a message to the patient 11 communicating that the caregiver has been summoned to help the patient. The controller 14 may also command the user interface 42 to provide an audio communication to the patient 11 that the caregiver has been summoned. Once the caregiver arrives at the patient 11, the caregiver engages the user interface 42 to let the controller 14 know the caregiver has arrived. In another example, the patient sensor unit 12 may see that a caregiver has arrived and communicate the information to the controller 14. In another example, a sensor included in the patient support apparatus 20 may determined that the caregiver has arrived and communicate the information to the controller 14.

In addition, the caregiver may request data from the hospital information system 28 using the user interface 42. The controller 14 receives the request from the user interface 42, obtains data from the hospital information system 28, and displays the data on the user interface 42 for the caregiver. The controller 14 may also receive other information from the hospital information system 28 which may be useful in the analysis of predicting future patient need.

Figure 3:
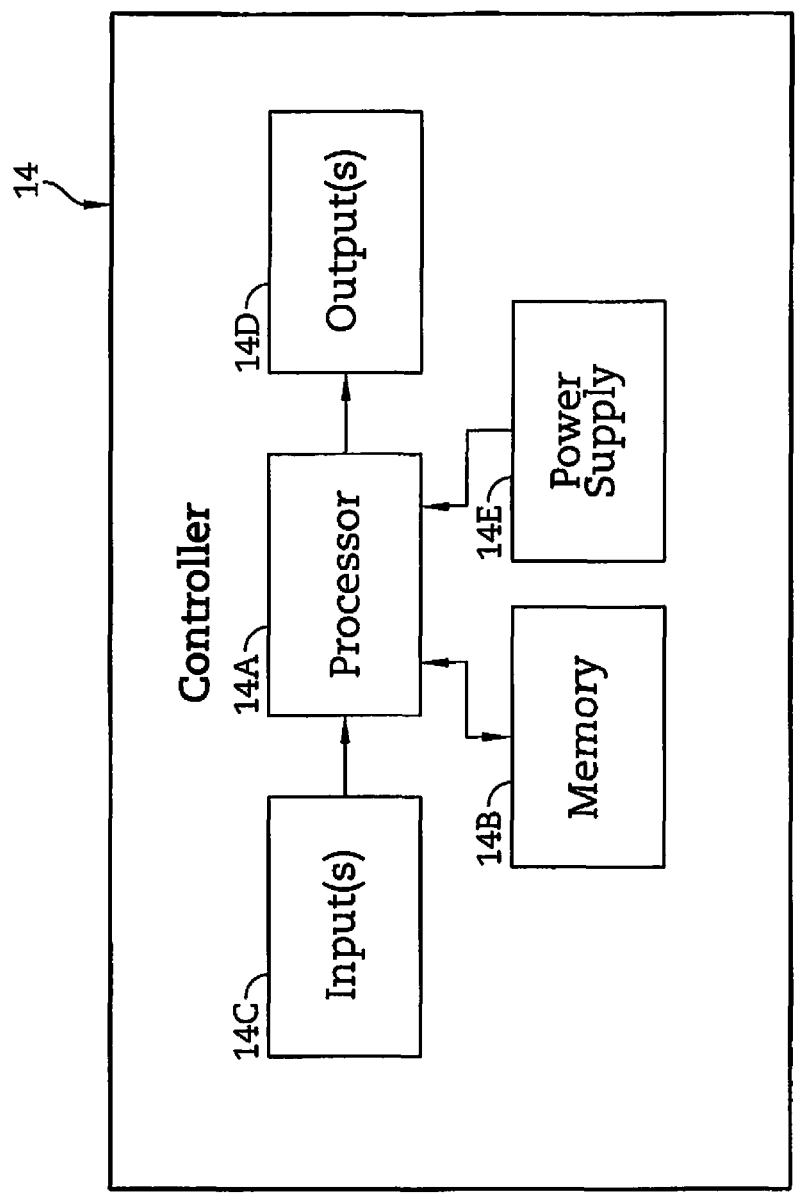
FIG. 3 is a diagrammatic view of a controller included in the patient-need prediction system of FIGS. 1 and 2.

The controller 14 includes a processor 14A, memory 14B, one or more inputs 14C, and one or more outputs 14D as shown in FIG. 3. Sensor information may be received by processor 14A via inputs 14C and stored in memory 14B. In addition, processor 14A may execute various processes, for example, the process 200. During execution of the process 200, the processor 14A issues various commands via outputs 14D. In one example, the processor 14A commands to the communication link 26 to summon a caregiver via the hospital information system 28. Outputs 14D of controller 14 may be coupled to actuators, blowers, equipment in the patient room 24, etc. to control various equipment and processes included in the patient-need prediction system 10 and patient support apparatus 20. The processor 14A may store information received from inputs 14C in memory 14B for additional processing, collection of additional data, or communication of data to the hospital information system 28.

As shown in FIG. 3, the controller 14 includes a power supply 14E. The power supply 14E may be a battery which supplies power to the processor 14A. The power supply 14E may also be a wire which is coupled to a power supply included in the patient support apparatus 20. The power supply 14E may also include a transformer which provides power from the patient support apparatus 20 or an electrical wall socket to the processor 14A at an appropriate voltage and frequency.

As discussed above, the controller 14 receives sensor signals from the patient sensor unit 12 as shown in FIG. 2. The processor 14A of the controller 14 executes instructions stored in memory 14B to perform the process 200 as shown in FIG. 4. The process 200 begins with an operation 202 which captures patient data obtained from the patient sensor signal provided by the patient sensor unit 12. The process 200 then proceeds to an operation 204 in which the processor 14A evaluates the patient data. During the operation 204, the processor 14A examines the patient data over time to look for differences in the patient data that may be predictive of patient stress or need.

In one example of the operation 204, the processor 14A compares a patient's facial expressions at a first time to a patient's facial expressions at a later second time. The controller 14 looks for micro-expressions (brief involuntary facial expressions) that are predictive of patient stress or need. In another example of the operation 204, the processor 14A compares a thermal image of the patient at a first time to a thermal image of the patient at a later second time. The controller 14 looks for increases in temperature of the patient that are indicative of blushing as provided by increased blood flow to the face, neck, and hands which may be predictive of patient stress or need. Other objective physiological responses which may be monitored by the patient sensor unit 12 includes increased skin temperature, increased heart rate, increased blood pressure, and increased perspiration. In addition, the controller 14 may retrieve information from the hospital information system 28 about medication or therapy administered to the patient 11. Such information may be used by the controller 14 to modify the analysis to take into account patient treatment information.

As shown, for example, in FIG. 4, the process 200 includes optional operations that may be executed in parallel with the operations 202 and 204. The process 200 includes an operation 206 in which the processor 14A captures bed data obtained from the bed sensor signal provided by the bed sensor unit 38. The process 200 then proceeds to an operation 208 in which the processor 14A evaluates the bed data. During the operation 208, the processor 14A examines the bed data for use in improving prediction of patient need and in predicting risk of fall for the patient 11. The bed data may also include data obtained from the hospital information system 28.

In one example of operation 208, the processor 14A evaluates an orientation of the support frame 32. If the support frame 32 is in a raised position, the risk of fall or injury from a fall is increased. If the support frame 32 is a lowered position, the risk of fall or injury is reduced as the patient has less distance to fall before impacting the floor. In another example of operation 208, the processor 14A evaluates a position of the side rails 36. If one or more of the side rails 36 are lowered, then the ability of the patient 11 to exit the patient support apparatus 20 is increased. If all of the side rails 36 are raised, then the ability of the patient 11 to exit the patient support apparatus 20 is decreased. Reference is hereby made to U.S. Provisional Patent Application No. 61/610,663, filed Mar. 14, 2012 and titled ALGORITHM FOR PREDICTING AND MITIGATING ADVERSE EVENTS for disclosure relating to additional data, factors, and information pertaining to mitigating adverse events, which application is hereby incorporated in its entirety herein.

After the process 200 has completed the operation 204, 208, the process 200 proceeds to an operation 210 as shown, for example, in FIG. 4. During operation 210, the processor 14A uses the evaluations performed during operations 204, 208 to determine a probability of patient need in a predetermined future time period. The probability may be expressed in terms of a percentage value. The processor may calculate the probability by adding up various components where each component is a value provided during the operations 204, 208 and multiplied by a weighing factor according to correlation or relationship to known patient need or stress. In one example, a probability of 100% indicates that the patient 11 is undergoing stress and is in immediate need of help from a caregiver. For example, the stress may result from a full bladder and an immediate need to perform a toileting function. A probability of less than 50% indicates that the patient 11 is undergoing stress and may have need of help from a caregiver in the future.

The operation 210 may also include a cost/benefit factor which provides for a cost/benefit analysis. The cost/benefit analysis weighs the burden of performing a predetermined action in the operation 216 with the benefits of early intervention. The performance of too many predetermined actions may lead to alarm fatigue resulting in caregivers not trusting the patient-need prediction system. As a result, the cost/benefit factor may change the overall threshold by examining other factors such as the likelihood of fall for the patient, risk for skin damage, etc. For some patients, caregivers may desire more false alarms because the risk to the patient of falling, for example, may outweigh some false alarms.

The process 200 then proceeds to a decision operation 214 as shown in FIG. 4. The decision operation 214 determines whether the probability calculated in the decision operation 210 has exceeded a predetermined threshold. The predetermined threshold may be a generic value set for all patients. However, the predetermined threshold may be a customized value specific to each patient. Furthermore, the predetermined value may be set according to factors associated with risk of incontinence or fall associated with each patient. The predetermined threshold may also be changed from time to time by the controller 14 in response to feedback provided by the bed sensor unit 38, the patient sensor unit 12, and the user interface 42. In this example, the threshold value may be changed as a result of making a prediction and determining that the prediction was either right or wrong. In another example, the threshold value may be changed after the controller 14 observes a known stress event and learns from the event to determine specific changes in the patient that was observed so that the threshold value is customized to a specific patient.

If the decision operation 214 determines that the probability threshold was not exceeded, the process 200 returns to operations 202 and 206 to capture additional patient and bed data. If the decision operation 214 determines that the probability threshold was exceeded, the process proceeds to an operation 216 in which controller 14 commands one or more predetermined actions to occur as shown in FIG. 4. In one example, the predetermined action includes the controller 14 commanding the communication link 26 to request that a caregiver come to help the patient 11 via the hospital information system 28 and the nurse call system 30. The predetermined action may further include the controller 14 commanding the user interface 42 to provide a notification to the patient 11 that a caregiver has been summoned to help the patient 11.

The process 200 also includes optional operations 218, 220 which may be performed if the optional operations 206, 208 related to bed data are performed. As shown in FIG. 4, the process 200 may proceed from the decision operation 214 if the probability threshold is exceeded to the operation 218. The operation 218 uses the evaluated bed data and evaluated patient data provided by the operations 204, 208 to determine a probability of fall for the patient 11. The probability may be expressed in terms of a percentage value. The processor may calculate the probability by adding up various components where each component is a value provided during the operations 204, 208 and multiplied by a weighing factor according to correlation or relationship to known patient risk of fall. In one example, a probability of 100% indicates that the patient 11 will fall if left to exit the patient support apparatus 20 without help from a caregiver. A probability of less than 50% indicates that the patient 11 is unsteady and may fall but is unlikely to fall.

The process 200 then proceeds to a decision operation 220 as shown in FIG. 4. The decision operation 220 determines whether the probability calculated in the decision operation 214 has exceeded a predetermined threshold. The predetermined threshold may be a generic value set for all patients. However, the predetermined threshold may be a customized value specific to each patient. Furthermore, the predetermined value may be set according to factors associated with risk of fall associated with each patient. The predetermined threshold may also be changed from time to time by the controller 14 in response to feedback provided by the bed sensor unit 38, the patient sensor unit 12, and the user interface 42. In this example, the threshold value may be changed as a result of making a prediction and determining that the prediction was either right or wrong.

If the decision operation 220 determines that the probability threshold was not exceeded, the process 200 returns to operations 202 and 206 to capture additional patient and bed data. If the decision operation 220 determines that the probability threshold was exceeded, the process proceeds to the operation 216 in which controller 14 commands one or more predetermined actions to occur as shown in FIG. 4. In another example where bed data is available to the controller, the predetermined action includes the controller 14 commanding the communication link 26 to request that a caregiver come to help the patient 11 via the hospital information system 28 and the nurse call system 30, commanding the user interface 42 to provide a notification to the patient 11 that a caregiver has been summoned to help the patient 11, and commanding that a siderail lock engage locking the side rails 36 in the raised position blocking the patient from exiting the patient support apparatus 20 until a caregiver arrives. Here, the risk of an incontinence event may be preferred to the risk of fall.

The controller 14 took the above described predetermined action as a result of the controller 14 examining several factors. First, the controller 14 determined that the probability threshold for patient need was exceeded and that that patient would likely attempt to the exit the patient support apparatus 20 for a toileting activity in a near future time frame. Second, the controller 14 also determined that the fall probability threshold was exceeded and that the patient was likely to fall if allowed to exit the patient support apparatus 20 without help from a caregiver. As a result, the controller 14 issued a command to block exit from the patient support apparatus 20 so that risk of fall could be minimized.

The controller 14 may also communicate with an environmental systems controller (not shown) which provides an interface between the patient-need prediction system 10 and various environmental systems including lights, heating-ventilating-air-conditioning system, and entertainment devices such as a television or radio, for example. The environmental systems controller may provide information to the controller 14 and act on instructions received from the controller 14 to modify operation of the environmental systems as part of the operation 216. Some of the information provided by the environmental systems controller is stored in memory associated with the environmental systems controller. The information provided by the environmental systems controller is updated as operating parameters of the environmental systems change. The controller 14 may issue commands to the environmental systems controller as part of the operation 216 to perform a predetermined action.

The controller 14 may also be in communication with one or more peripheral devices positioned in the patient room 24. The peripheral devices each perform a therapy or diagnostic function. For example, the peripheral device may be a ventilator, heart monitor, blood pressure monitor, infusion device, blood oxygen monitor, sequential compression device, high-frequency chest wall oscillation device, or another standalone diagnostic or therapeutic device. Information used by the controller 14 may be stored in memory associated with a peripheral device, including the therapy parameters or current operating conditions of the peripheral device. In addition, diagnostic values such as a heart rate, blood pressure, or other diagnostic values may be stored in memory associated with the peripheral device. In some cases, the peripheral devices may communicate to the controller 14 via a network connection such as a controller area network (CAN) and information stored on a controller of the device may be accessible by the controller. In other cases, the information may be stored by the hospital information system 28. In still other cases, the peripheral devices may communicate with the controller 14 and the controller 14 may store information related to the operator of the peripheral device(s) in memory 14B of the controller 14. Any number of peripheral devices may be in communication with the patient-need prediction system 10. It should be understood that peripheral devices may be in direct communication with the hospital information system 28 without being connected through the patient-need prediction system 10 or the patient support apparatus 20. The controller 14 may use data obtained from the peripheral devices to improve the operations 204, 208 so that improved predictions may occur.

The nurse call system 30 generates alarms and notifies caregivers of alarm conditions based on signals from the controller 14 of the patient-need prediction system 10. The user interface 42 of the patient-need prediction system 10 may be used to provide communication, such as audio or video communications, between the patient 11 and a nurse positioned at a central nurse call station. Caregivers may also carry communication badges that include telephone or other voice communication capability, with the badges providing a direct communication between the caregiver and the central nurse call station or the patient 11, such as the system disclosed in U.S. Pat. No. 7,746,218 titled CONFIGURABLE SYSTEMS FOR ALERTING CAREGIVERS, incorporated by reference herein. The nurse call system and/or communication badges may facilitate direct communication between a caregiver and the patient 11 located in the care facility. In this way, the nurse call system 30 acts as a dispatch system to provide instructions to caregivers when the controller 14 issues commands as part of the operation 216.

Once the operation 216 is complete, the process 200 returns to the operations 202, 206. There, the process 200 starts over and data from the patient sensor unit 12 and the bed sensor unit 38 is collected.

Figure 5:
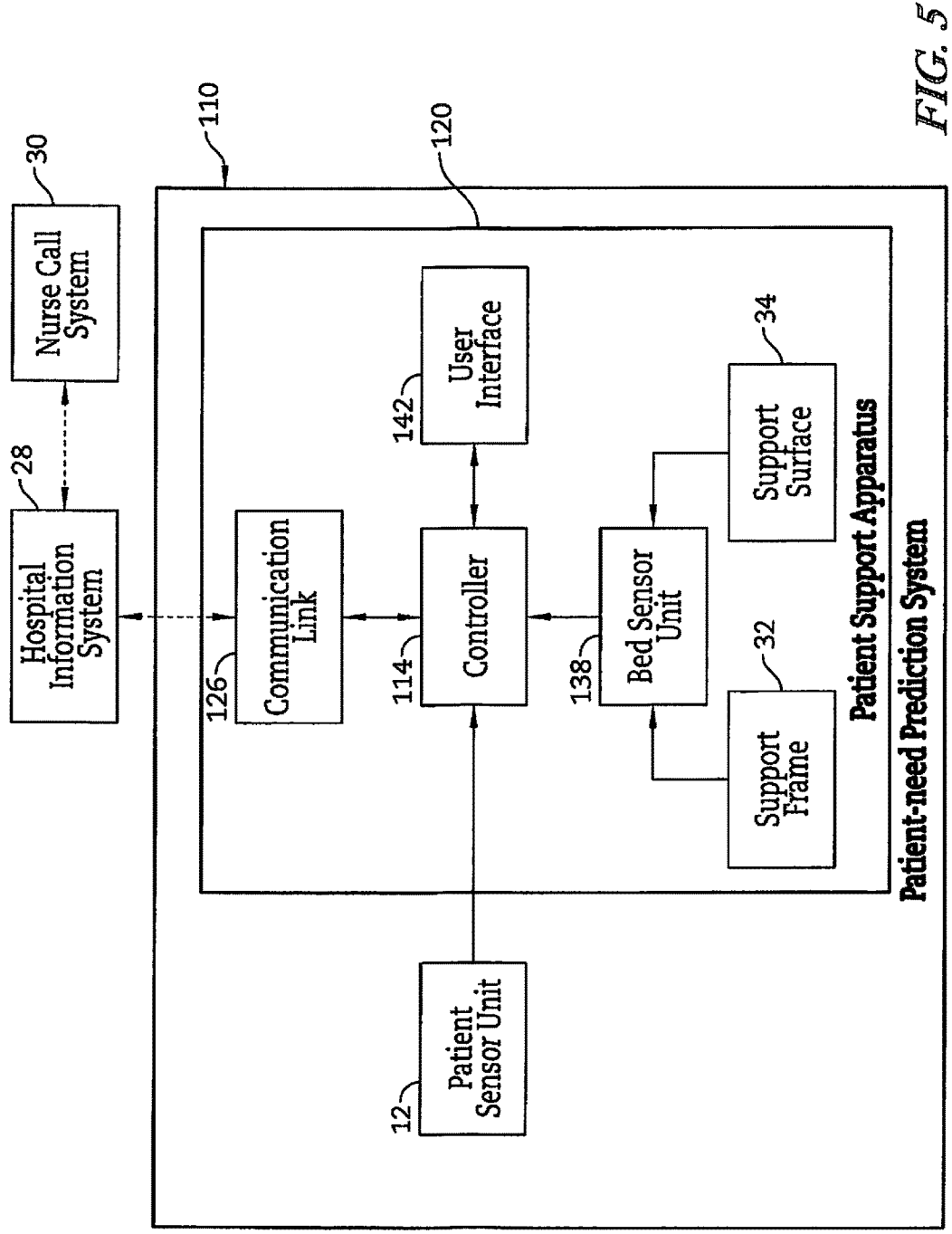
FIG. 5 is a diagrammatic view of a second embodiment of a patient-need prediction system in accordance with the present disclosure.

Another embodiment of a patient-need prediction system 110 is shown, for example, in FIG. 5. The patient-need prediction system 110 includes the patient sensor unit 12 and a patient support apparatus 120. In this illustrative embodiment, the patient support apparatus 120 includes a controller 114, a communication link 126, a user interface 142, a bed sensor unit 138, the support frame 32, and patient support surface 34 as well as other equipment. The patient support apparatus 120 provides the bed sensor unit 138, the controller 114, the user interface 142, and the communication link 126. The bed sensor unit 138, the controller 114, the user interface 142, and the communication link 126 function substantially the same as discussed above and will not be discussed in detail.

The controller 114 is configured to execute the process 200 as described above. Here, the controller 114 is able to integrate the bed sensor signal provided by the bed sensor unit 138 as the bed sensor unit 138 is included in the patient support apparatus 120. As an example, all sensors included in the patient support apparatus may be part of the bed sensor unit 138 and have sensor signals included in the bed sensor signal. As a result, any sensor data available from the patient support apparatus 20 is available to the patient-need prediction system 110.

The controller 14 of the patient support apparatus 120 includes inputs 14C that provide information to the processor 14A. These inputs 14C may be one or more sensors included in the patient support apparatus 120. For example, frame position sensors, siderail position sensors, support surface sensors, a scale system, and caster brake sensors are all in communication with the controller 14. The frame position sensors provide information regarding the position of various components of the patient support apparatus 120. Information provided may include the height of the patient support apparatus, the inclination of a head section of the support frame 32, the degree of tilt of an upper frame included in the support frame, or any other frame position data that might be available from frame position sensors of the particular patient support apparatus 120.

The side rail position sensors provide an indication to the controller 14 of whether a particular side rail 36 of the patient support apparatus 120 is in a raised or lowered position. It is contemplated that additional sensors may be implemented which indicate whether a particular side rail is latched into a particular position. The patient support apparatus 120 may includes siderail actuators, siderail locks, and caster brake actuators which are each controlled by the controller 14. For example, the patient support apparatus 120 may include motorized side rails such as those disclosed in U.S. Patent Application Publication No. US 2009/0229051, titled SIDERAIL FOR A PATIENT-SUPPORT APPARATUS, which is incorporated by reference herein. The patient support apparatus 120 may also include locking side rails that include an electromechanical lock, such as those disclosed in U.S. Patent No. US 2009/0229051, with the lock retaining the side rail in a particular position. The siderail actuators are operable to move the siderails between raised and lowered positions. The siderail locks are operable to lock the siderail in a given position. The caster brake actuators are operable to activate the caster brake system. For example, the caster brake actuators may actuate a locking mechanism. For example, the structures disclosed in U.S. Pat. No. 7,690,059 titled HOSPITAL BED or U.S. Pat. No. 7,200,894 titled ROLLER, each of which is hereby incorporated by reference herein, disclose suitable locking mechanisms. The controller 14 may command one or more pieces of the above discussed equipment to engage or disengage as part of a predetermined action during the operation 216.

The support surface sensors provide information regarding the operation of the patient support surface 34, such as an inflatable/pneumatic mattress, of the patient support apparatus 120. Such a patient support surface 34 may be integrated into the support frame 32 of the patient support apparatus 120 or may be a separate structure that is operated generally independently of the patient support apparatus 120, but communicates with the controller 14 of the patient support apparatus 120.

The support surface sensors may include pressure sensors that identify pressures in particular inflatable structures of the support surface or they may include position sensors. For example, accelerometers positioned in particular locations within the patient support surface 34 may provide feedback regarding the amount of inclination of a particular section of the patient support surface 34 relative to gravity, independent of the frame position sensors. The support surface sensors may also provide information regarding the degree of lateral rotation of a patient supported on the support surface. In addition, the patient support apparatus 120 may include a support surface pressure control system which is operable to control the pressure in one or more air bladders in the patient support surface 34. Information from the support surface sensors may be included in the bed sensor signal and used to improve determination of probabilities during the operations 210, 218.

The scale system provides information to the controller 14 regarding the weight of the patient supported on the patient support apparatus 120. The scale system also provides information regarding the position of a patient on the patient support apparatus 120 and may provide information regarding the degree of movement of the patient. Such a system is disclosed in U.S. Pat. No. 5,276,432 titled PATIENT EXIT DETECTOR MECHANISM FOR HOSPITAL BED or U.S. Pat. No. 7,437,787 titled LOAD-CELL BASED HOSPITAL BED CONTROL, each of which is incorporated herein by reference. The data from the scale system may also be used by the controller 14 to determine if an unexpected weight has been added to the patient support apparatus 120 or provide other data regarding activities around the patient support apparatus 120. For example, in an approach disclosed in U.S. Published Pat. Application No. 2008/0189865 titled SYSTEM AND METHOD FOR CONTROLLING AN AIR MATTRESS, which is incorporated herein by reference, the support surface sensors and the scale system cooperate to provide data regarding the position of a patient supported on the patient support apparatus 120. For example, the support surface sensors and scale system may cooperate to determine that a patient is sitting up on a patient support apparatus 120 without having the head section raised as disclosed in U.S. Published Pat. Application No. 2008/0189865. Such information may be useful during the operation 218 to help determine the probability of bed exit by the patient 11.

The caster brake sensors provide information to the controller 14 regarding the position of the brakes on the patient support apparatus 120. For example, casters should be in a locked position to prevent the patient support apparatus 120 from rolling as the patient 11 attempts to exit the patient support apparatus 120. In addition, activation or deactivation of the caster brake sensors may provide an indication of the presence of a caregiver in the patient room 24 at a particular time. Activation of other caregiver controls may be considered to identify the presence of a caregiver in the patient room 24 when the controls are activated on the user interface 42.

It is within the scope of this disclosure for the patient support apparatus 120 to include other sensors that provide information to the controller 14 regarding the status of portions of the patient support apparatus 120 and the sensors discussed herein are examples only. In general, information that is related to the patient 11 is considered to be physiological information, data items, or factors. This may include diagnostic or therapy information from a peripheral device, diagnoses or physical characteristics available from the hospital information system 28, including medications being taken or therapies being received, or patient specific information as detected by the scale system or support surface sensors.

Information related to the patient support apparatus 120 is considered to be patient support apparatus information, data items, or factors. These include the positions of members or components of the patient support apparatus 120, the type of patient support apparatus, the status of patient support apparatus functions such as a caster lock or siderail lock.

Information related to the environment as determined and controlled by the environmental system is considered to be environmental information, data items, or factors. This may include the status of various environmental equipment including room temperature, the status of lighting, the status of entertainment devices or other similar information.

The invention claimed is:

1. A method for predicting patient needs comprising:
   detecting electromagnetic radiation from a field of view and providing a signal indicative of a characteristic of a patient in the field of view, the signal being based on the electromagnetic radiation; and
   processing the signal to produce a value related to a stress condition experienced by the patient located in the field of view to determine whether a patient need is indicated by the value related to a stress condition experienced by the patient and to perform a predetermined action if the patient need is predicted.

2. A method for predicting patient needs comprising:
   detecting electromagnetic radiation from a field of view and providing a signal indicative of a characteristic of a patient in the field of view, the signal being based on the electromagnetic radiation;
   detecting a status of equipment included in a patient support apparatus supporting the patient; and
   processing the signal to produce a value related to a stress condition experienced by the patient located in the field of view to determine whether a patient need is indicated by the value related to a stress condition experienced by the patient and to perform a predetermined action if the patient need is predicted.

3. A method for predicting patient needs comprising:
   detecting electromagnetic radiation from a field of view and providing a patient signal indicative of a characteristic of a patient in the field of view, the signal being based on the electromagnetic radiation;
   detecting a status of a component of a patient support apparatus; and
   processing the signal to produce a value related to a stress condition experienced by the patient located in the field of view to determine whether the value has exceeded a predetermined limit and to perform a predetermined action if the value has exceeded the predetermined limit.

4. The method for predicting patient needs of claim 1, wherein the electromagnetic radiation is visual light and the sensor unit detects the visual light over time.

5. The method for predicting patient needs of claim 4, wherein the field of view is limited to a face of the patient in the field of view and the characteristic of the patient in the field of view is a change in a facial expression of the patient that is indicative of the stress condition.

6. The method for predicting patient needs of claim 4, wherein the characteristic of the patient in the field of view is a change in color of a patient's skin indicative of the stress condition.

7. The method for predicting patient needs of claim 4, wherein the characteristic of the patient in the field of view is a change in position of the patient in the field of view indicative of the stress condition.

8. The method for predicting patient needs of claim 7, wherein the stress condition is at least one of a need to urinate and defecate by the patient.

9. The method for predicting patient needs of claim 1, wherein the electromagnetic radiation is infrared light.

10. The method for predicting patient needs of claim 9, wherein the characteristic of the patient in the field of view is a patient's skin temperature as measured by the infrared light.

11. The method for predicting patient needs of claim 10, wherein the stress condition is at least one of a need to urinate and defecate by the patient.

12. The method for predicting patient needs of claim 11, wherein the sensor unit is a camera located in spaced-apart relation to the patient in the field of view.

13. The method for predicting patient needs of claim 1, further comprising the step of providing a bed-sensor signal indicative of a status of equipment included in a patient support apparatus supporting the patient.

14. The method for predicting patient needs of claim 13, further comprising the step of processing the bed-sensor signal and the patient sensor signal to produce the value related to the stress condition experience by the patient located in the field of view as detected by the sensor unit.

15. The method for predicting patient needs of claim 14, wherein the patient support apparatus includes a support frame, a support surface supported by the support frame, and a moveable side rail coupled to the support frame to move relative to the support frame between a raised position and a lowered position and the bed-sensor signal is indicative of the position of the movable side rail.

16. The method for predicting patient needs of claim 14, wherein the patient support apparatus includes a support frame and a support surface supported by the support frame, and the bed-sensor signal is indicative of a pressure exerted on the support surface when the patient is resting on the support surface.

17. The method for predicting patient needs of claim 1, further comprising the step of communicating with a hospital information system.

18. The method for predicting patient needs of claim 17, wherein the predetermined action includes requesting via the communication link for a caregiver to come to the patient within a predetermined time period.

19. The method for predicting patient needs of claim 17, further comprising the step of providing a communication via the user interface to the patient that a caregiver has been requested to come to the patient within the predetermined time period.

20. The method for predicting patient needs of claim 18, wherein the communication is visual and displayed on a display included in the user interface.

21. The method for predicting patient needs of claim 19, wherein the communication is auditory and emitted through a speaker included in the user interface.

22. The method for predicting patient needs of claim 1, wherein the predetermined action includes commanding the light to emit light.

* * * * *